US007522980B2

(12) United States Patent
Watkins et al.

(10) Patent No.: US 7,522,980 B2

(45) Date of Patent: Apr. 21, 2009

(54) TELEMATICS BASED VEHICLE MAINTENANCE CLIENT NOTIFICATION

(75) Inventors: Gary A. Watkins, Royal Oak, MI (US); Michael J. Devereux, Oakland Township, MI (US); Jon M. Brancheau, Snellville, GA (US)

(73) Assignee: General Motors Corporation, Detroit, MI (US)

( * ) Notice: Subject to any disclaimer, the term of this patent is extended or adjusted under 35 U.S.C. 154(b) by 4 days.

(21) Appl. No.: 10/740,876

(22) Filed: Dec. 19, 2003

(65) Prior Publication Data

US 2005/0137763 A1 Jun. 23, 2005

(51) Int. Cl.
*G01N 33/26* (2006.01)

(52) U.S. Cl. ........................................ 701/33; 340/457

(58) Field of Classification Search .................. 701/33, 701/29, 30, 24, 34, 101; 340/425.5, 457, 340/438, 457.4, 450.3, 450, 450.2; 73/112, 73/53.05, 117.3

See application file for complete search history.

(56) References Cited

U.S. PATENT DOCUMENTS 4,306,525 A * 12/1981 Faxvog .................... 123/196 S
4,677,847 A * 7/1987 Sawatari et al. ............ 73/53.05
5,750,887 A * 5/1998 Schricker ................... 73/117.3
5,781,871 A * 7/1998 Mezger et al. .............. 455/424
5,931,878 A * 8/1999 Chapin, Jr. ................... 701/30
5,969,601 A * 10/1999 Sato et al. ................ 340/450.3
6,222,445 B1 * 4/2001 Beckhusen .................. 340/457
6,429,773 B1 * 8/2002 Schuyler .................. 340/425.5
6,609,051 B2 * 8/2003 Fiechter et al. ............... 701/33
6,901,788 B2 * 6/2005 Han et al. .................. 73/53.05
2004/0203974 A1 * 10/2004 Seibel ....................... 455/517

OTHER PUBLICATIONS

Kelly Carroll, Data to ride shotgun: InfoMove helps connect cars to Internet, Telephony Dec. 13, 1999, Copyright 1999 by Primedia Business Magazines & Media Inc., "All Rights Reserved", Telephony, Spectrum; ISSN: 0040-2656, 1091 words.

Seattle, InfoMove Delivers New Generation of Wireless Internet Services for the Car, Business Wire, Oct. 18, 1999, Copyright 1999 Business Wire, Inc. Business Wire, Business Editors/Technology Writers, 994 words.

(Continued)

*Primary Examiner*—Dalena Tran

(57) ABSTRACT

The present invention provides a method for providing vehicle maintenance client notification within a telematics equipped mobile vehicle that includes monitoring the mobile vehicle for vehicle system maintenance information, determining an oil-life value based on the vehicle system maintenance information, determining when the oil-life value exceeds at least one oil-life threshold level, sending the vehicle system maintenance information to a call center responsive to the oil-life threshold level determination, and generating a service reminder, at the call center, based on the received vehicle system maintenance information. The step of determining when the oil-life value exceeds the oil-life threshold level may include comparing the determined oil-life value with the at least one oil-life threshold level, determining at least one oil-life threshold level that is exceeded by the oil-life value, and initiating a vehicle data upload based on the at least one exceeded oil-life threshold level.

21 Claims, 3 Drawing Sheets

OTHER PUBLICATIONS

Bob Low, Motoring in the new millennium on the Net, Daily Record, May 1, 1998, Copyright 1998 Scottish Daily Record & Sunday Mail Ltd., Daily Record May 1, 1998, Friday, p. 31 Road, 734 words.

Tarre Beach, New Products; Sidebar, Wireless Review Apr. 1, 2000, Copyright 2000 by Primedia Business Magazines & Media Inc., "All rights Reserved" Wireless Review, Apr. 1, 2000, New Products; ISSN: 1099-9248, 351 words.

Flint, Mich., Jan.3, BUIC XP2000—A Concept Cat For The 21$^{ST}$ Century, PR Newswire, Jan. 3, 1995, Copyright 1995 PR Newswire Association, Inc. PR Newswire, Jan. 3, 1995, Tuesday, Financial News, (With Photo) To Business and Auto Editors, 2149 words.

U.S. Appl. No. 11/618,253, filed Dec. 29, 2006, Brad T. Reeser / "Vehicle Fleet Email Notification Method and System".

U.S. Appl. No. 11/618,198, filed Dec. 29, 2006, Chester A. Huber et al. / "Vehicle Email Notification Using Data From Different Sources".

U.S. Appl. No. 11/618,222, filed Dec. 29, 2006, Fahd Laghrari / "Enrollment Method for a Vehicle Email Notification System".

U.S. Appl. No. 11/618,237, filed Dec. 29, 2006, Krishnaraj Inbarajan / Vehicle Email Notification with Regional-Specific Content.

U.S. Appl. No. 11/618,186, filed Dec. 29, 2006, Shane McCutchen et al. / "Vehicle Email Notification System and Method".

* cited by examiner

TELEMATICS BASED VEHICLE MAINTENANCE CLIENT NOTIFICATION

FIELD OF THE INVENTION

This invention relates generally to wireless communications with a mobile vehicle. More specifically, the invention relates to a method and system for implementing vehicle maintenance client notification within a telematics equipped vehicle.

BACKGROUND OF THE INVENTION

The opportunity to utilize wireless features in a mobile vehicle is ever increasing as the automobile is being transformed into a communications and entertainment platform as well as a transportation platform. Wireless features include wireless vehicle communication, networking, maintenance and diagnostic services for a mobile vehicle.

Typically, conventional wireless systems within mobile vehicles (e.g. telematics units) provide voice communication. Recently, these wireless systems have been utilized to update systems within telematics units, such as, for example radio station presets. Other systems within mobile vehicles, such as, for example a power train control may be updated as well. Information may also be collected from systems and subsystems within mobile vehicles and provided to a vehicle manufacturer for analysis, such as, for example system usage, component wear, and the like. One example of component wear and associated maintenance includes periodic system maintenance, such as, oil maintenance. Currently, most consumers perform oil maintenance, such as, for example oil changes utilizing predetermined maintenance recommendations or programs. Unfortunately, scheduled oil changes may not coincide with actual use or realistic oil life and can result in oil being utilized in an inefficient manner.

The present invention advances the state of the art.

SUMMARY OF THE INVENTION

One aspect of the invention includes a method for operating a telematics unit within a mobile vehicle including monitoring the mobile vehicle for vehicle system maintenance information, determining an oil-life value based on the vehicle system maintenance information, determining when the oil-life value exceeds at least one oil-life threshold level, sending the vehicle system maintenance information to a call center responsive to the oil-life threshold level determination, and generating a service reminder, at the call center, based on the received vehicle system maintenance information.

In accordance with another aspect of the invention, a computer readable medium storing a computer program includes: computer readable code for monitoring the mobile vehicle for vehicle system maintenance information; computer readable code for determining an oil-life value based on the vehicle system maintenance information; computer readable code for determining when the oil-life value exceeds at least one oil-life threshold level; computer readable code for sending the vehicle system maintenance information to a call center responsive to the oil-life threshold level determination; and computer readable code for generating a service reminder, at the call center, based on the received vehicle system maintenance information.

In accordance with yet another aspect of the invention, a system for operating a telematics unit within a mobile vehicle is provided. The system includes means for monitoring the mobile vehicle for vehicle system maintenance information. The system additionally includes means for determining an oil-life value based on the vehicle system maintenance information. Means for determining when the oil-life value exceeds at least one oil-life threshold level is provided. Means for sending the vehicle system maintenance information to a call center responsive to the oil-life threshold level determination and means for generating a service reminder, at the call center, based on the received vehicle system maintenance information is also provided.

The aforementioned, and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

DETAILED DESCRIPTION OF THE DRAWINGS

Figure 1:
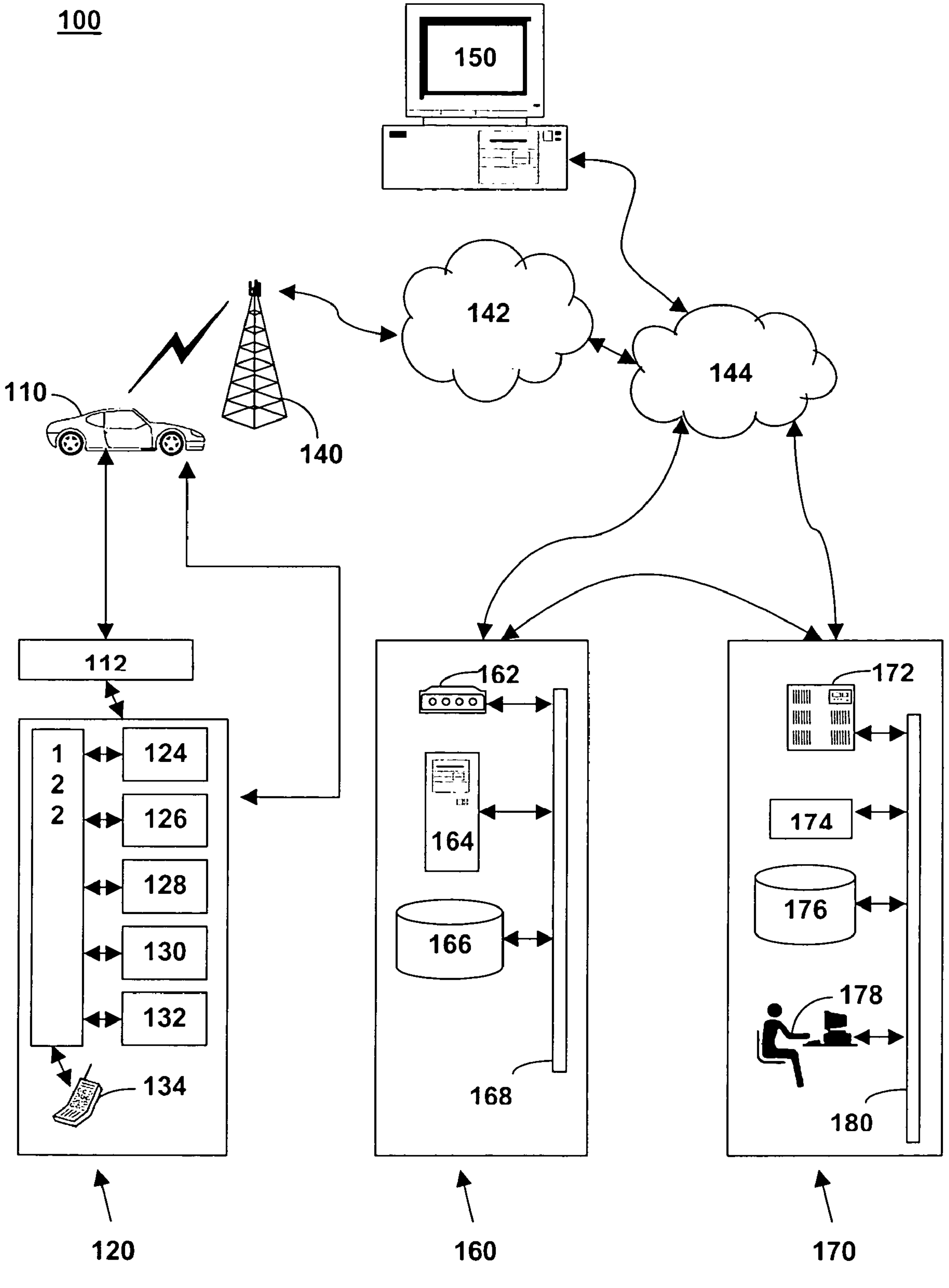
FIG. 1 illustrates an operating environment for implementing wireless communication within a mobile vehicle communication system.

FIG. 1 illustrates one embodiment of system for data transmission over a wireless communication system, in accordance with the present invention at 100. Mobile vehicle communication system (MVCS) 100 includes a mobile vehicle communication unit (MVCU) 110, a vehicle communication network 112, a telematics unit 120, one or more wireless carrier systems 140, one or more communication networks 142, one or more land networks 144, one or more client, personal or user computers 150, one or more web-hosting portals 160, and one or more call centers 170. In one embodiment, MVCU 110 is implemented as a mobile vehicle equipped with suitable hardware and software for transmitting and receiving voice and data communications. MVCS 100 may include additional components not relevant to the present discussion. Mobile vehicle communication systems and telematics units are known in the art.

MVCU 110 may also be referred to as a mobile vehicle throughout the discussion below. In operation, MVCU 110 may be implemented as a motor vehicle, a marine vehicle, or as an aircraft. MVCU 110 may include additional components not relevant to the present discussion.

MVCU 110, via a vehicle communication network 112, sends signals to various units of equipment and systems (detailed below) within MVCU 110 to perform various functions such as unlocking a door, opening the trunk, setting personal comfort settings, and calling from telematics unit 120. In facilitating interactions among the various communication and electronic modules, vehicle communication network 112 utilizes network interfaces such as controller-area network (CAN), International Organization for Standardization (ISO) Standard 9141, ISO Standard 11898 for high-speed applications, ISO Standard 11519 for lower speed applications, and Society of Automotive Engineers (SAE) Standard J1850 for high-speed and lower speed applications.

MVCU 110, via telematics unit 120, sends and receives radio transmissions from wireless carrier system 140. Wireless carrier system 140 is implemented as any suitable system for transmitting a signal from MVCU 110 to communication network 142.

Telematics unit 120 includes a digital signal processor (DSP) 122 connected to a wireless modem 124, a global positioning system (GPS) unit 126, an in-vehicle memory 128, a microphone 130, one or more speakers 132, and an embedded or in-vehicle mobile phone 134. In other embodiments, telematics unit 120 may be implemented without one or more of the above listed components, such as, for example GPS unit 126 or speakers 132. Telematics unit 120 may include additional components not relevant to the present discussion.

In one embodiment, DSP 122 is implemented as a microcontroller, controller, host processor, or vehicle communications processor. In another embodiment, DSP 122 is implemented as a processor working in conjunction with a central processing unit (CPU) performing the function of a general purpose processor. GPS unit 126 provides longitude and latitude coordinates of the vehicle responsive to a GPS broadcast signal received from a one or more GPS satellite broadcast systems (not shown). In-vehicle mobile phone 134 is a cellular-type phone, such as, for example an analog, digital, dual-mode, dual-band, multi-mode or multi-band cellular phone.

DSP 122 executes various computer programs that control programming and operational modes of electronic and mechanical systems within MVCU 110. DSP 122 controls communications (e.g. call signals) between telematics unit 120, wireless carrier system 140, and call center 170. In one embodiment, a voice-recognition application is installed in DSP 122 that can translate human voice input through microphone 130 to digital signals. DSP 122 generates and accepts digital signals transmitted between telematics unit 120 and a vehicle communication network 112 that is connected to various electronic modules in the vehicle. In one embodiment, these digital signals activate the programming mode and operation modes, as well as provide for data transfers. In this embodiment, signals from DSP 122 are translated into voice messages and sent out through speaker 132.

Communication network 142 includes services from one or more mobile telephone switching offices and wireless networks. Communication network 142 connects wireless carrier system 140 to land network 144. Communication network 142 is implemented as any suitable system or collection of systems for connecting wireless carrier system 140 to MVCU 110 and land network 144.

Land network 144 connects communication network 142 to client computer 150, web-hosting portal 160, and call center 170. In one embodiment, land network 144 is a public-switched telephone network (PSTN). In another embodiment, land network 144 is implemented as an Internet protocol (IP) network. In other embodiments, land network 144 is implemented as a wired network, an optical network, a fiber network, other wireless networks, or any combination thereof. Land network 144 is connected to one or more landline telephones. Communication network 142 and land network 144 connect wireless carrier system 140 to web-hosting portal 160 and call center 170.

Client, personal or user computer 150 includes a computer usable medium to execute Internet browser and Internet-access computer programs for sending and receiving data over land network 144 and optionally, wired or wireless communication networks 142 to web-hosting portal 160. Personal or client computer 150 sends user preferences to web-hosting portal through a web-page interface using communication standards such as hypertext transport protocol (HTTP), and transport-control protocol and Internet protocol (TCP/IP). In one embodiment, the data includes directives to change certain programming and operational modes of electronic and mechanical systems within MVCU 110. In operation, a client utilizes computer 150 to initiate setting or re-setting of user-preferences for MVCU 110. User-preference data from client-side software is transmitted to server-side software of web-hosting portal 160. User-preference data is stored at web-hosting portal 160.

Web-hosting portal 160 includes one or more data modems 162, one or more web servers 164, one or more databases 166, and a network system 168. Web-hosting portal 160 is connected directly by wire to call center 170, or connected by phone lines to land network 144, which is connected to call center 170. In an example, web-hosting portal 160 is connected to call center 170 utilizing an IP network. In this example, both components, web-hosting portal 160 and call center 170, are connected to land network 144 utilizing the IP network. In another example, web-hosting portal 160 is connected to land network 144 by one or more data modems 162. Land network 144 sends digital data to and from modem 162, data that is then transferred to web server 164. Modem 162 may reside inside web server 164. Land network 144 transmits data communications between web-hosting portal 160 and call center 170.

Web server 164 receives user-preference data from user computer 150 via land network 144. In alternative embodiments, computer 150 includes a wireless modem to send data to web-hosting portal 160 through a wireless communication network 142 and a land network 144. Data is received by land network 144 and sent to one or more web servers 164. In one embodiment, web server 164 is implemented as any suitable hardware and software capable of providing web services to help change and transmit personal preference settings from a client at computer 150 to telematics unit 120 in MVCU 110. Web server 164 sends to or receives from one or more databases 166 data transmissions via network system 168. Web server 164 includes computer applications and files for managing and storing personalization settings supplied by the client, such as door lock/unlock behavior, radio station preset selections, climate controls, custom button configurations and theft alarm settings. For each client, the web server potentially stores hundreds of preferences for wireless vehicle communication, networking, maintenance and diagnostic services for a mobile vehicle.

In one embodiment, one or more web servers 164 are networked via network system 168 to distribute user-preference data among its network components such as database 166. In an example, database 166 is a part of or a separate computer from web server 164. Web server 164 sends data transmissions with user preferences to call center 170 through land network 144.

Call center 170 is a location where many calls are received and serviced at the same time, or where many calls are sent at the same time. In one embodiment, the call center is a telematics call center, facilitating communications to and from telematics unit 120 in MVCU 110. In an example, the call center is a voice call center, providing verbal communications between an advisor in the call center and a subscriber in a mobile vehicle. In another example, the call center contains each of these functions. In other embodiments, call center 170 and web-hosting portal 160 are located in the same or different facilities.

Call center 170 contains one or more voice and data switches 172, one or more communication services managers 174, one or more communication services databases 176, one or more communication services advisors 178, and one or more network systems 180.

Switch 172 of call center 170 connects to land network 144. Switch 172 transmits voice or data transmissions from call center 170, and receives voice or data transmissions from telematics unit 120 in MVCU 110 through wireless carrier system 140, communication network 142, and land network 144. Switch 172 receives data transmissions from and sends data transmissions to one or more web-hosting portals 160. Switch 172 receives data transmissions from or sends data transmissions to one or more communication services managers 174 via one or more network systems 180.

Communication services manager 174 is any suitable hardware and software capable of providing requested communication services to telematics unit 120 in MVCU 110. Communication services manager 174 sends to or receives from one or more communication services databases 176 data transmissions via network system 180. Communication services manager 174 sends to or receives from one or more communication services advisors 178 data transmissions via network system 180. Communication services database 176 sends to or receives from communication services advisor 178 data transmissions via network system 180. Communication services advisor 178 receives from or sends to switch 172 voice or data transmissions.

Communication services manager 174 provides one or more of a variety of services, including enrollment services, navigation assistance, directory assistance, roadside assistance, business or residential assistance, information services assistance, emergency assistance, and communications assistance. Communication services manager 174 receives service-preference requests for a variety of services from the client via computer 150, web-hosting portal 160, and land network 144. Communication services manager 174 transmits user-preference and other data to telematics unit 120 in MVCU 110 through wireless carrier system 140, communication network 142, land network 144, voice and data switch 172, and network system 180. Communication services manager 174 stores or retrieves data and information from communication services database 176. Communication services manager 174 may provide requested information to communication services advisor 178.

In one embodiment, communication services advisor 178 is implemented as a real advisor. In an example, a real advisor is a human being in verbal communication with a user or subscriber (e.g. a client) in MVCU 110 via telematics unit 120. In another embodiment, communication services advisor 178 is implemented as a virtual advisor. In an example, a virtual advisor is implemented as a synthesized voice interface responding to requests from telematics unit 120 in MVCU 110.

Communication services advisor 178 provides services to telematics unit 120 in MVCU 110. Services provided by communication services advisor 178 include enrollment services, navigation assistance, real-time traffic advisories, directory assistance, roadside assistance, business or residential assistance, information services assistance, emergency assistance, and communications assistance. Communication services advisor 178 communicate with telematics unit 120 in MVCU 110 through wireless carrier system 140, communication network 142, and land network 144 using voice transmissions, or through communication services manager 174 and switch 172 using data transmissions. Switch 172 selects between voice transmissions and data transmissions.

As used herein, the word "exceeds" includes a broad definition, and includes both levels increasing beyond a predetermined limit, as well as levels decreasing below a predetermined limit.

Figure 2:
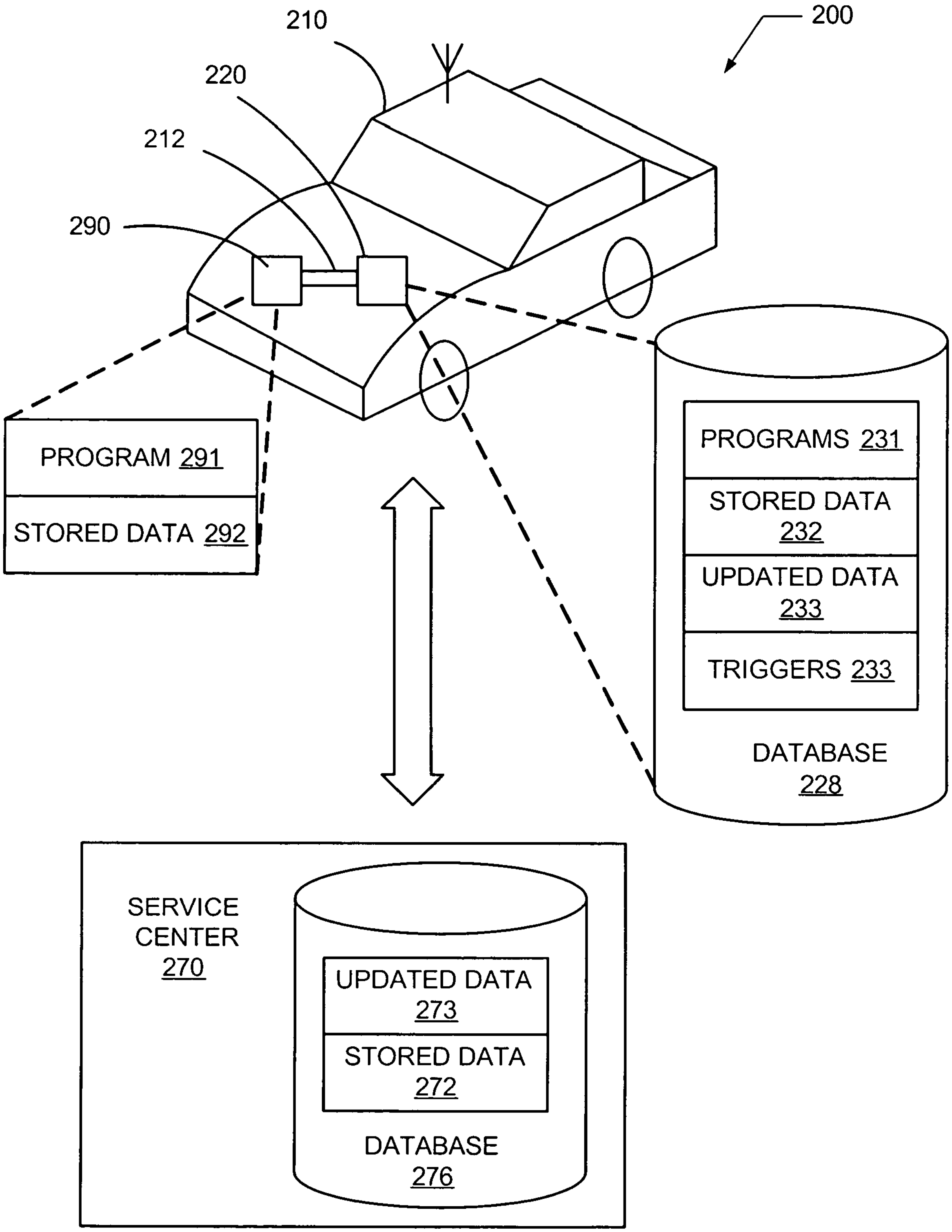
FIG. 2 is a block diagram of telematics based programming gateway in accordance with an embodiment of the present invention.

FIG. 2 is a block diagram of a telematics based programming gateway in accordance with an embodiment of the present invention. FIG. 2 shows a telematics based programming gateway system 200 for providing vehicle maintenance client notification to a mobile vehicle. In FIG. 2, the programming gateway system includes a mobile vehicle 210 having a telematics device 220 coupled to one or more vehicle system modules 290 via a vehicle communication bus 212, and a telematics service center 270, such as, for example a call center. Telematics device 220 further includes a database 228 that contains programs 231, stored data 232, updated data 233 and triggers 234. The vehicle system module 290 further includes a program 291 and stored data 292. The service center 270 further includes a database 276 containing updated data 273, and stored data 272. Telematics based programming gateway system 200 may include additional components not relevant to the present discussion.

Telematics device 220 is any telematics device enabled for operation with a telematics service provider, such as, for example telematics device 120 as described with reference to FIG. 1. Telematics device 220 in vehicle 210 is in communication with telematics service center 270. Telematics device 220 includes volatile and non-volatile memory components for storing data and programs. In one embodiment, memory components in telematics device 220 contain database 228.

Database 228 includes one or more programs 231 for operating telematics device 220, such as, for example, for managing vehicle maintenance client notification. A program module receives vehicle system maintenance information at updated data 233. In an example, the vehicle system maintenance information is cached within updated data 233. The vehicle system maintenance information is stored at stored data 232. In one embodiment, telematics device 220 acts as a data cache for vehicle system maintenance information, caching any received vehicle system maintenance information that is provided to a vehicle system module 290 for the telematics device.

Vehicle system module (VSM) 290 is any vehicle system control module having software and hardware components for operating, controlling or monitoring one or more vehicle systems. In one embodiment, vehicle system module 290 is a controller for controlling a vehicle system such as, for example, a power train control module (PCM). In another embodiment, vehicle system module 290 is a controller for receiving vehicle system maintenance information from a vehicle system such as, for example, the aforementioned PCM or an odometer module. Additional examples of vehicle system modules 290 include diagnostic modules, brake system modules, fluid level modules, fuel consumption monitoring modules, pollution control modules, stability control modules, climate control modules, and the like.

Vehicle system module 290 contains one or more processors, one or more memory devices and one or more connection ports. In one embodiment, VSM 290 includes a software switch for scanning received information to identify that data has been received. VSM 290 is coupled to a vehicle communication bus 212, and therefore to any other device that is also coupled to vehicle communication bus 212. The vehicle communication bus is also referred to as a vehicle communication network. In one embodiment, VSM 290 is directly coupled to telematics device 220, such as, for example vehicle communication bus 212 coupling telematics device 220 to vehicle system modules 290. In an example, vehicle communication bus 212 is a vehicle communication network 112 as described in FIG. 1, above. In another embodiment, VSM 290 is indirectly coupled to telematics device 220.

VSM 290 includes one or more programs 291 and stored data 292 stored in memory. In one embodiment, program 291 includes software for receiving vehicle system maintenance information and storing the received vehicle system maintenance information at stored data 292.

Telematics service center 270 is any service center providing telematics services, such as, call center 170 described with reference to FIG. 1. In one embodiment, service center 270 includes hardware and software for managing vehicle maintenance client notification within database 276. In another embodiment, service center 270 is configured to access a database 276 that is in another location but coupled to service center 270 such as, for example, database 176 in web server 160 as described in FIG. 1.

Database 276 contains records of mobile vehicle maintenance stored at stored data 272. Database 276 receives data from sources, such as, for example telematics device 220 at updated data 273. In an example, database 276 receives vehicle system maintenance information at updated data 273. In one embodiment, database 276 is a relational database that includes information such as, for example, vehicle makes and models, vehicle systems for the makes and models, individual vehicle identification numbers (VIN) and other vehicle identifiers, and recommended vehicle servicing.

In operation, VSM 290 monitors mobile vehicle 210 for vehicle system maintenance information. In one embodiment, VSM 290 determines an oil-life value based on the vehicle system maintenance information. In another embodiment, VSM 290 sends the vehicle system maintenance information to telematics device 220 for processing. In this embodiment, telematics device 220 determines an oil-life value based on the vehicle system maintenance information. In an example, the oil-life value determination is an ongoing real-time determination based on one of the aforementioned embodiments. In another embodiment, the oil-life value determination is a periodic determination based on one of the aforementioned embodiments.

When the determined oil-life value exceeds one or more oil-life threshold levels, a vehicle data upload is initiated based on the at least one exceeded oil-life threshold level. In one embodiment, the oil-life threshold levels are located in event triggers 234. The vehicle system maintenance information is sent to service center 270. In one embodiment, the vehicle system maintenance information is retrieved from stored data 232 and updated data 233.

Service center 270 manages the compilation and delivery of service reminders based on the one or more oil-life threshold levels that are exceeded by the determined oil-life value as well as other service reminders that are generated as a result of the vehicle system maintenance information. Examples of service reminders include oil servicing, brake servicing, pollution control system servicing, stability control system servicing (e.g. shock absorbers), climate control system servicing (e.g. air conditioning), power train system servicing (e.g. transmission), and the like. In one embodiment, the service reminder indicates a vehicle service is recommended. In another embodiment, the service reminder indicates a vehicle service is not recommended. In an example, if oil servicing is determined to not be necessary at a given mileage point (e.g. 3000 miles) based on the determined oil-life value, a service reminder indicating a vehicle service is not recommended at the present time can be produced by the service center.

Service center 270 sends service reminders to telematics device 220 within mobile vehicle 210. In one embodiment, mobile vehicle 210 receives the service reminders and displays the service reminders for a client, such as, for example via a user interface, an automated virtual advisor/agent, and the like. The client can then act on the provided service reminders.

Figure 3:
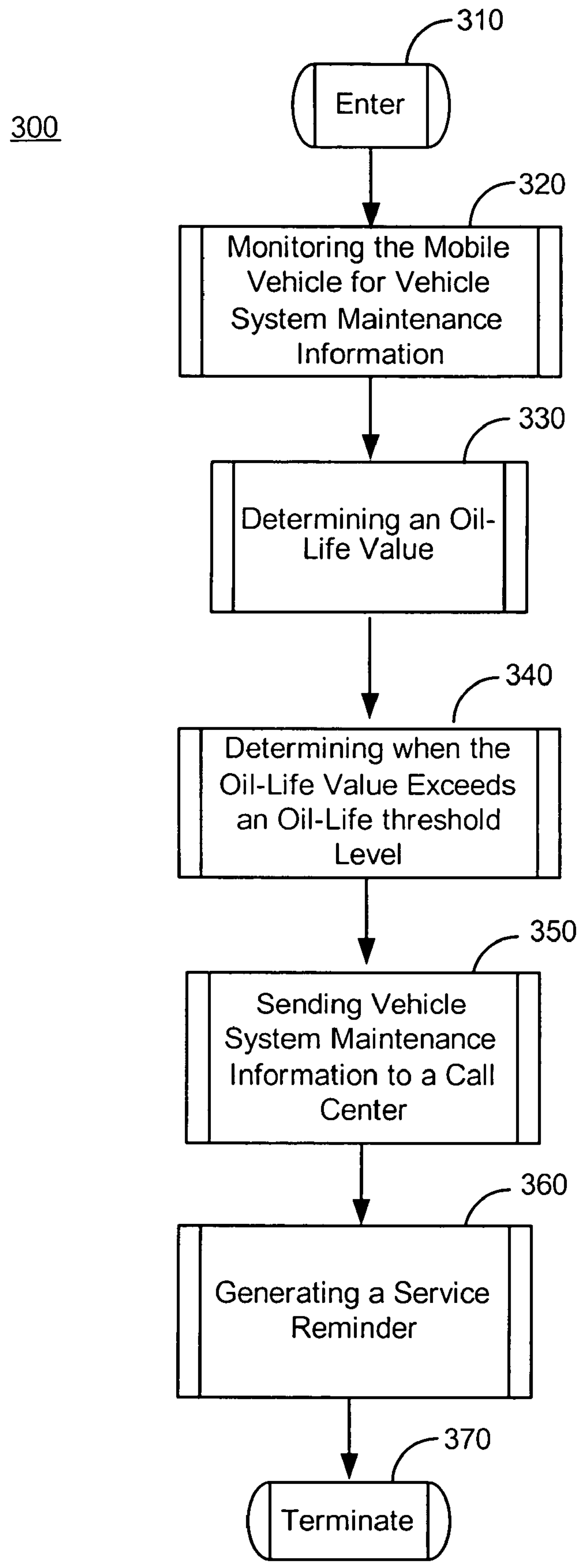
FIG. 3 is a flow diagram of one embodiment of a method of implementing vehicle maintenance client notification in a telematics unit, in accordance with the present invention.

FIG. 3 is a flow diagram of an embodiment of a method of providing vehicle maintenance client notification. In FIG. 3, method 300 may utilize one or more systems detailed in FIGS. 1 and 2, above. The present invention can also take the form of a computer usable medium including a program for configuring an electronic module within a vehicle. The program stored in the computer usable medium includes computer program code for executing the method steps described in FIG. 3. In FIG. 3, method 300 begins at step 310.

At step 320, a mobile vehicle is monitored for vehicle system maintenance information. Examples of vehicle system maintenance information include odometer information, diagnostic information, brake system information, fluid level information, fuel consumption information, pollution control system information, stability control system information, climate control system information, vehicle lighting system information, power train system information, and the like. In one embodiment, monitoring the mobile vehicle for vehicle system maintenance information includes receiving the vehicle system maintenance information and storing the received vehicle system maintenance information. In an example and referring to FIG. 2 above, VSM 290 monitors mobile vehicle 210 for vehicle system maintenance information.

At step 330, an oil-life value is determined based on the vehicle system maintenance information. In one embodiment, the oil-life value is a variable oil-life performance metric. In an example, the oil-life value is determined from several measured parameters including but not limited to vehicle type, engine type, application, and the like. The measured parameters are determined based upon measurements, such as, but not limited to viscosity, opacity, and the like.

At step 340, a determination is made as to whether the oil-life value exceeds at least one oil-life threshold level. In one embodiment, determining when the oil-life value exceeds the oil-life threshold level includes comparing the determined oil-life value with the at least one oil-life threshold level, determining at least one oil-life threshold level that is exceeded by the oil-life value, and initiating a vehicle data upload based on the at least one exceeded oil-life threshold level. In an example, the vehicle data upload includes vehicle system maintenance information associated with the at least one exceeded oil-life threshold level.

In one embodiment, the at least one oil-life threshold level is a pre-selected level, such as, for example a manufacturer selected level. In another embodiment, the at least one oil-life threshold level is configurable, such as, for example an oil-life threshold level that is configurable at any time throughout the life of the mobile vehicle.

At step 350, the vehicle system maintenance information is sent to a call center responsive to the oil-life threshold level determination. In one embodiment, the vehicle system maintenance information is sent to a call center responsive to the oil-life threshold level determination as described in FIG. 1, above.

At step 360, a service reminder is generated at the call center based on the received vehicle system maintenance information. In one embodiment, a service center manages the compilation of service reminders based on the one or more oil-life threshold levels that are exceeded by the determined oil-life value as well as other service reminders that are generated as a result of the vehicle system maintenance information. In an example and referring to FIG. 2 above, service center 270 manages the compilation of service reminders based on the one or more oil-life threshold levels that are exceeded by the determined oil-life value as well as other service reminders that are generated as a result of the vehicle system maintenance information. Examples, of service reminders include oil servicing, brake servicing, pollution control system servicing, stability control system servicing (e.g. shock absorbers), climate control system servicing (e.g. air conditioning), power train system servicing (e.g. transmission), and the like.

At step 370, the method ends.

In another embodiment, method 300 further includes receiving the service reminder at the telematics unit. In one embodiment, a service center manages the delivery of service reminders based on the one or more oil-life threshold levels that are exceeded by the determined oil-life value as well as other service reminders that are generated as a result of the vehicle system maintenance information. In an example and referring to FIG. 2 above, service center 270 manages the delivery of service reminders based on the one or more oil-life threshold levels that are exceeded by the determined oil-life value as well as other service reminders that are generated as a result of the vehicle system maintenance information.

In another embodiment, the service center sends service reminders to a telematics device within a mobile vehicle. In this embodiment, the mobile vehicle receives the service reminders and displays the service reminders for a client, such as, for example via a user interface. The client can then act on the provided service reminders. In an example and referring to FIG. 2 above, service center 270 sends service reminders to telematics device 220 within mobile vehicle 210. In this example, mobile vehicle 210 receives the service reminders and displays the service reminders for a client, such as, for example via a user interface as described in FIG. 1, above. The client can then act on the provided service reminders.

The above-described methods and implementation for providing vehicle maintenance client notification are example methods and implementations. These methods and implementations illustrate one possible approach for providing vehicle maintenance client notification within a telematics equipped mobile vehicle. The actual implementation may vary from the method discussed. Moreover, various other improvements and modifications to this invention may occur to those skilled in the art, and those improvements and modifications will fall within the scope of this invention as set forth in the claims below.

The present invention may be embodied in other specific forms without departing from its spirit or essential characteristics. The described embodiments are to be considered in all respects only as illustrative and not restrictive.

What is claimed is:

1. A method for operating a telematics unit within a mobile vehicle, the method comprising:

monitoring the mobile vehicle for vehicle system maintenance information;

determining an oil-life value based on the vehicle system maintenance information;

determining whether the oil-life value exceeds at least one oil-life threshold level;

sending information associated with the vehicle system maintenance information to a call center via a wireless carrier system;

generating a service reminder, at the call center, based on the received information, that a vehicle service is recommended, if the oil-life value exceeds the at least one oil-life threshold level; and generating a service reminder, at the call center, based on the received information, that a vehicle service is not recommended, if the oil-life value does not exceed the at least one oil-life threshold level and the mobile vehicle has attained a given mileage.

2. The method of claim 1, further comprising:

receiving the service reminder at the telematics unit.

3. The method of claim 1, wherein the vehicle system maintenance information is selected from one or more of the group consisting of: oil viscosity, oil opacity, vehicle type and engine type.

4. The method of claim 1, wherein monitoring the mobile vehicle for vehicle system maintenance information comprises:

receiving the vehicle system maintenance information; and storing the received vehicle maintenance information.

5. The method of claim 1, wherein the oil-life value is a variable oil-life performance metric.

6. The method of claim 1, wherein determining whether the oil-life value exceeds the at least one oil-life threshold level comprises:

comparing the determined oil-life value with the at least one oil-life threshold level;

determining at least one oil-life threshold level that is exceeded by the oil-life value; and initiating a vehicle data upload based on the at least one exceeded oil-life threshold level.

7. The method of claim 6, wherein the vehicle data upload includes vehicle system maintenance information associated with the at least one exceeded oil-life threshold level.

8. The method of claim 1, wherein the at least one oil-life threshold level is a pre-selected level.

9. The method of claim 1, wherein the at least one oil-life threshold level is configurable.

10. The method of claim 1 wherein determining the oil-life value based on the vehicle system maintenance information comprises measuring oil viscosity.

11. The method of claim 1 wherein determining the oil-life value based on the vehicle system maintenance information comprises measuring oil opacity.

12. A computer readable medium for operating a telematics unit within a mobile vehicle, comprising:

computer readable code for monitoring the mobile vehicle for vehicle system maintenance information;

computer readable code for determining an oil-life value based on the vehicle system maintenance information;

computer readable code for determining whether the oil-life value exceeds at least one oil-life threshold level;

computer readable code for sending information associated with the vehicle system maintenance information to a call center via a wireless carrier system computer readable code for generating a service reminder, at the call center, based on the received information, that a vehicle service is recommended, if the oil-life value exceeds the at least one oil-life threshold level; and computer readable code for generating a service reminder, at the call center, based on the received information, that a vehicle service is not recommended, if the oil-life value does not exceed the at least one oil-life threshold level and the mobile vehicle has attained a given mileage.

13. The computer readable medium of claim 12, further comprising:

computer readable code for implementing a received service reminder at the telematics unit.

14. The computer readable medium of claim 12, wherein the vehicle system maintenance information is selected from one or more of the group consisting of: oil viscosity, oil opacity, vehicle type and engine type.

15. The computer readable medium of claim 12, wherein the computer readable code for monitoring the mobile vehicle for vehicle system maintenance information comprises:

computer readable code for identifying received vehicle system maintenance information; and computer readable code for storing the received vehicle system maintenance information.

16. The compute readable medium of claim 12, wherein the oil-life value is a variable oil-life performance metric.

17. The computer readable medium of claim 12, wherein determining when the oil-life value exceeds the at least one oil-life threshold level comprises:

computer readable code for comparing the determined oil-life value with the at least one oil-life threshold level;

computer readable code for determining at least one oil-life threshold level that is exceeded by the oil-life value; and computer readable code for initiating a vehicle data upload based on the at least one exceeded oil-life threshold level.

18. The computer readable medium of claim 17, wherein the vehicle data upload includes vehicle system maintenance information associated with the at least one exceeded oil-life threshold level.

19. The computer readable medium of claim 12, wherein the at least one oil-life threshold level is a pre-selected level.

20. The computer readable medium of claim 12, wherein the at least one oil-life threshold level is configurable.

21. A system for operating a telematics unit within a mobile vehicle, the system comprising:

means for monitoring the mobile vehicle for vehicle system maintenance information;

means for determining an oil-life value based on the vehicle system maintenance information;

means for determining whether the oil-life value exceeds at least one oil-life threshold level;

means for sending information associated with the vehicle system maintenance information to a call center via a wireless carrier system;

means for generating a service reminder, at the call center, based on the received information, that a vehicle service is recommended, if the oil-life value exceeds the at least one oil-life threshold level, and that a vehicle service is not recommended, if the oil-life value does not exceed the at least one oil-life threshold level and the mobile vehicle has attained a given mileage.

* * * * *